United States Patent
Carale et al.

(10) Patent No.: US 6,447,758 B1
(45) Date of Patent: Sep. 10, 2002

(54) CATIONIC ANTIBACTERIAL DENTIFRICE EXHIBITING SUPERIOR FOAMING PROPERTIES

(75) Inventors: M. Teresa R. Carale, Princeton, NJ (US); Susan M. Herles, Flemington, NJ (US); Thomas Boyd, Somerset, NJ (US); Michael Prencipe, West Windsor, NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 09/847,819

(22) Filed: May 2, 2001

(51) Int. Cl.$^7$ .............................. A61K 7/16; A61K 7/22
(52) U.S. Cl. ........................................... 424/54; 429/49
(58) Field of Search ....................... 424/49–58

(56) References Cited

U.S. PATENT DOCUMENTS

| | | | | |
|---|---|---|---|---|
| 4,211,341 A | * | 7/1980 | Weyn | 222/94 |
| 4,487,757 A | * | 12/1984 | Kiozpeoplov | 424/49 |
| 4,632,825 A | * | 12/1986 | Ferlauto et al. | 424/52 |
| 4,701,318 A | * | 10/1987 | Ferlauto et al. | 424/52 |
| 4,774,077 A | * | 9/1988 | Ferlauto et al. | 424/52 |
| 5,320,829 A | * | 6/1994 | Garlich et al. | 424/54 |
| 5,565,190 A | * | 10/1996 | Santalucia et al. | 424/53 |
| 5,599,525 A | * | 2/1997 | Hsu et al. | 424/49 |
| 5,820,853 A | * | 10/1998 | Glandorf | 424/52 |
| 5,820,854 A | * | 10/1998 | Glandorf | 424/52 |
| 5,980,869 A | * | 11/1999 | Sanker et al. | 424/58 |
| 6,086,856 A | * | 7/2000 | Saferstein et al. | 424/58 |
| 6,283,336 B1 | * | 9/2001 | Dwyer et al. | 222/190 |

* cited by examiner

Primary Examiner—Shep K. Rose
(74) Attorney, Agent, or Firm—Paul Shapiro

(57) ABSTRACT

A dual component antiplaque oral composition having superior foaming properties in which a first component contains a cationic antibacterial agent and the second component contains a anionic surfactant normally incompatible with the cationic antibacterial agent, the first and second components are simultaneously combined for application to the teeth, the first and second components being physically segregated prior to use, the components when mixed upon application to teeth providing substantially unimpaired antiplaque effect with superior foaming properties.

5 Claims, No Drawings

CATIONIC ANTIBACTERIAL DENTIFRICE EXHIBITING SUPERIOR FOAMING PROPERTIES

BACKGROUND OF THE INVENTION

1. Field of the Invention

The present invention relates to an oral care composition which contains a cationic antibacterial compound effective in retarding bacterial plaque accumulation on teeth and more particularly to a dual component dentifrice composition containing a cationic antibacterial compound which achieves plaque reduction with superior foaming characteristics.

2. The Prior Art

Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of antibacterial agents have been suggested in the art to retard plaque formation and the oral infections and dental disease associated with plaque formation. For example, cationic antibacterial compounds such as cetyl pyridinium chloride are well known to the art for their antibacterial activity and have been used in oral compositions to counter plaque formation by bacterial accumulation in the oral cavity. However, these compounds present a problem when formulated in a dentifrice in that they are deactivated by traditional anionic surfactants such as sodium lauryl sulfate. Stable, clinically effective dental formulations have been made with quaternary ammonium compounds and nonionic surfactants, but these formulations are very poor foamers and result in inferior products.

Anionic surfactants, such as sodium lauryl sulfate (SLS) are conventionally included in oral formulations, to provide solubilization, dispersion, emulsification and wetting of the other ingredients present, especially flavor oils. Further, these surfactants are extremely effective in providing a cosmetic effect in promoting the foaming of the oral composition. Oral compositions with strong foaming ability are preferred by consumers, since it is perceived that the greater the foaming, the better the composition cleans the tooth and other oral surfaces, removing stain, plaque and debris therefrom.

There is a clear need in the art to formulate a dentifrice product capable of delivering a cationic antibacterial agent effective in the retardation of bacterial plaque accumulation on teeth whereby the surfactant present in the dentifrice imparts strong foaming characteristics to the dentifrice composition without inhibiting the bioavailability of the antibacterial compound.

SUMMARY OF THE INVENTION

The present invention encompasses a dual component dental composition which when applied to teeth contains a combination of a cationic antibacterial compound, and an anionic surfactant ingredient normally incompatible with the antibacterial compound whereby reduction of plaque is accomplished during tooth brushing accompanied by a superior foaming benefit.

The present invention is based upon the discovery that when a separately maintained first cationic antibacterial compound containing dental component which is free of an anionic surfactant ingredient and a second anionic surfactant containing dentifrice component, which surfactant is normally incompatible with the antibacterial containing component, are simultaneously combined and thereafter applied to the surface of the teeth, an undiminished antiplaque efficacy is unexpectedly obtained with superior foaming properties when the teeth are brushed with the combined components.

In one embodiment of the present invention, a dual component dentifrice composition of the present invention is provided which is comprised of separate cationic antibacterial compound and anionic surfactant containing paste components which are housed in a container wherein the components are maintained separate from each other and are not combined and admixed until simultaneous application to teeth is to be performed by the user as by brushing. Unexpectedly, when the separately maintained dental components are contacted with each other immediately prior to application to teeth, the anionic surfactant does not appreciably immediately react to inactivate the antiplaque efficacy of the cationic antibacterial compound, thereby allowing the cationic antibacterial compound in its full efficacious form, to be applied to the teeth simultaneously in the presence of an anionic surfactant which imparts strong foaming characteristics to the combined dentifrice components.

DESCRIPTION OF THE PREFERRED EMBODIMENTS

In the practice of the present invention the dental component containing the cationic antibacterial agent ingredient is formulated as a paste using a vehicle containing a safe and effective amount of the cationic antibacterial compound.

Cationic antibacterial agents useful in the practice of the present invention are well known in the art. See, for instance the section on "Quaternary Ammonium and Related Compounds" in the article on "Antiseptics and Disinfectants" in Kirk-Othmer Encyclopedia of Chemical Technology, $2^{nd}$ edition (vol. 2, pp. 632–635), incorporated herein by reference. Cationic compounds which possess antibacterial activity (i.e., are germicides) are used against bacteria and have been used in oral compositions to counter plaque formation caused by bacteria in the oral cavity.

Among the most common of these antibacterial antiplaque quaternary ammonium compounds is benzethonium chloride, or diisobutylphenoxyethoxyethyl dimethyl benzyl ammonium chloride, and cetyl pyridinium chloride. In a dentifrice preparation this material is highly effective in promoting oral hygiene by reducing the formation of dental plaque and calculus, which is generally accompanied by a reduction in periodontal diseases.

Other antibacterial antiplaque quaternary ammonium compounds useful in the practice of the present invention include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, cetyl pyridinium chloride and quaternized 5-amino-1,3-bis(2-ethylhexyl)-5-methyl hexa hydropyrimidine are typical quaternary ammonium antibacterial agents.

The cationic antibacterial agent is included in the dentifrice component at a concentration of about 0.10 to about 1.5% by weight and preferably about 0.3 to about 1.2% by weight.

Anionic surfactants useful in the practice of the present invention include long chain fatty or ploy-lower alkoxy groups plus hydrophilic radicals. They will usually be in the form of salts, especially water soluble salts of alkali metals. Useful anionic surfactants include the higher fatty acid monoglyceride monosulfates, such as the sodium salts of the monosulfated monoglycerides of hydrogenated coconut oil fatty acid; higher alkyl sulfates, such as sodium lauryl sulfate; higher alkyl aryl sulfonates, such as sodium linear dodecyl benzene sulfonate; higher olefin sulfonates, such as sodium higher olefin sulfonate in which the olefin group is 12 to 21 carbon atoms; higher alkyl alkali sulfoacetates such as sodium lauryl sulfoacetate; higher fatty acid esters of 1,2-dihydroxypropane sulfonates; the substantially saturated higher aliphatic acyl amides of lower aliphatic aminocarboxylic acid alkali metal salts, such as those having 12 to 16 carbon atoms in the fatty acyl radicals; higher alkyl poly-lower alkoxy (of 10 to 100 alkoxies) sodium sulfates; higher fatty acid sodium and potassium soaps of coconut oil and tallow, and the like. The anionic surfactant, sodium lauryl sulfate, is preferred in the practice of the present invention.

The anionic surfactant is incorporated in the dentifrice component at a concentration of about 1.0 to about 5.0% by weight and preferably about 2.0 to about 3.0% by weight.

The individual dentifrice components are prepared as a paste prepared using a vehicle which contains water, humectant and thickener. The humectant is generally a mixture of humectants, such as glycerin, sorbitol and a polyethylene glycol of a molecular weight in the range of 200–1000, but other mixtures of humectants and single humectants may also be employed. The humectant content is in the range of about 10% to about 80% by weight and preferably about 10–30% by weight. The water content is in the range of about 10 to about 30% by weight.

Thickeners which may be used in the preparation of the abrasive paste component include natural and synthetic gums such as carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose. The thickener may be incorporated in the abrasive containing dentifrice component of the present invention at a concentration of about 0.1 to about 3% by weight and preferably about 0.5 to about 1.5% by weight.

Agents effective against dental calculus such as pyrophosphate salts including the mono, di, tri and tetra alkali metal and ammonium pyrophosphate and tripolyphosphate salts is still another additional ingredient which may be present in the antiplaque paste component of the present invention. Such agents are used in amounts sufficient to reduce calculus and are preferably in amounts which will release about 1% by weight $P_2O_7$ ion and most preferably at least about 1.3% by weight $P_2O_7$ ion.

Anionic polycarboxylate polymers having a molecular weight of about 1,000 to about 5,000.000, preferably about 30,000 to about 500,000 in the form of their free acids or preferably partially or more preferably fully neutralized water soluble alkali metal (e.g. potassium and preferably sodium) or ammonium salts are included in the oral composition of the present invention to enhance the anticalculus efficacy of the pyrophosphate salts. Preferred anionic polycarboxylate polymers are 1:4 to 4:1 copolymers of maleic anhydride or acid with another polymerizable ethylenically unsaturated monomer, preferably methyl vinyl ether/maleic anhydride having a molecular weight (M.W.) of about 30,000 to abut 1,000,000, most preferably about 30,000 to about 500,000. These copolymers are available, for example, under the trade designation Gantrez AN 139 (M.W. 500,000), AN 119 (M.W. 250,000); preferably Gantrez S-97 Pharmaceutical Grade (M.W. 70,000), or GAF Corporation.

Fluorine-providing salts having anti-caries efficacy may also be incorporated in the abrasive dentifrice component of the present invention and are characterized by their ability to release fluoride ions in water. Among these materials are alkali metal salts, for example, sodium fluoride, potassium fluoride, sodium fluorosilicate, and sodium monofluorophosphate. It is preferable to employ a fluoride salt to release about 10–1500 ppm of fluoride ion.

Any suitable flavoring or sweetening material may also be incorporated in the abrasive containing dentifrice component of the present invention. Examples of suitable flavoring constituents are flavoring oils, e.g., oils of spearmint, peppermint, wintergreen, sassafras, clove, sage, eucalyptus, marjoram, cinnamon, lemon and orange and methyl salicylate. Suitable sweetening agents include sucrose, lactose, maltose, sorbitol, xylitol, sodium cyclamate, perillartine and sodium saccharin. Suitably, flavor and sweetening agents may together comprise from 0.01% to 5% by weight or more of the abrasive containing dentifrice and at such concentrations render the combined gel and dentifrice components with a palatability acceptable to the user.

A striped dentifrice product is obtained in accordance with the practice of the present invention wherein colorants of contrasting colors are incorporated in each of the dentifrice components used in the practice of the present invention, the colorants being pharmacologically and physiologically nontoxic when used in the suggested amounts. Colorants used in the practice of the present invention include pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C # Yellow 15 lake. The pigments have a particle size in the range of 5–1000 microns, preferably 250–500 microns, and are present at a concentration of 0.5 to 3% by weight.

The dyes used in the practice of the present invention are generally food color additive presently certified under the Food Drug & Cosmetic Act for use in food and ingested drugs, including dyes such as FD&C Red #3 (sodium salts of tetraiodofluorescein), FD&C Yellow #5 (sodium slat of 4-p-sulfophenylaxo-B-naphtol-6-monosulfonate), FD&C Green #3 (disodium salt of 4-{[4-(n-ethyl-p-sulfobenzylamino)-phenyl]-4-hydroxy-2-sulfoniumphenyl)-methylene}-[1-(N-ethyl-N-p-sulfobenzy)-3,5-cyclohexadienimine], FD&C Blue #1 (disodium salt of disulfonic acid of indigotin) and mixtures thereof in various proportions. The concentration of the dye for the most effective result in the present invention is present in the abrasive containing dentifrice composition in an amount from about 0.0005% to about 2% by weight.

To prepare the separate dentifrice paste components of the present invention, the humectant and thickener are dispersed in a conventional mixer until the mixture becomes a slurry which is smooth in appearance, after which water is added. This mixture is heated to 100–130° F. and mixed for 10 to 30 minutes producing a homogeneous gel phase. Sweetener and color are added and mixed for 20 minutes. The mixture is transferred to a vacuum mixer and the abrasive is added and mixed for 10 to 30 minutes at high speed under a vacuum in the range of 5 to 100 millimeter of mercury pressure, preferably 5 to 50 mm Hg, providing a homogeneous mixture. The surfactant or antibacterial agent and flavor are then added to the mixture which is followed by mixing another 10 to 20 minutes under vacuum of 5 to 50 mm Hg. The resultant product is dentifrice paste of a texture like that of normal toothpastes having a pH in the range of 5 to 8, preferably 6.5 to 7.5, e.g., 7, and of satisfactory flavor.

The dual component composition of the present invention is packaged in a suitable dispensing container such as a tube or pump in which the components are maintained physically separated and from which the separated components may be dispensed synchronously. Such containers are known to the art. Examples of suitable pump devices are disclosed in U.S. Pat. Nos. 4,528,180 and 5,332,124. Examples of a suitable dispensing tube are disclosed in U.S. Pat. Nos. 4,487,757 and 4,687,663 wherein the tube is formed from a collapsible plastic web and is provided with a partition within the tube defining separate compartments in which the physically separated components are stored and from which they are dispersed through a suitable dispensing outlet.

The following specific Example illustrates the present invention. The individual gel and paste components described below were prepared by following the procedure described above. The amounts of the various ingredients are by weight unless otherwise indicated. The resultant components were packaged in tubes or other containers provided with means for physical separation of the individual dentifrice components.

EXAMPLE I

A series of dentifrice components containing the cationic antibacterial agent cetyl pyridinium chloride and different abrasive ingredients designated components A, B, C and D were prepared. These dentifrice components were then combined with a separately prepared second dentifrice component containing the anionic surfactant sodium lauryl sulfate designated component E and F. The ingredients of each of these dentifrice components are listed in Table I below.

TABLE I

| Ingredients | CPC Dentifrice Components (Wt. %) | | | | SLS Dentifrice Component (Wt. %) | |
|---|---|---|---|---|---|---|
| | A | B | C | D | E | F |
| Glycerin | 22.0 | 22.0 | 20.0 | 20.0 | 11.4 | — |
| Sorbitol | — | — | 20.85 | 20.85 | 23.7 | 57.937 |
| Polyethylene glycol 600 | — | — | 3.0 | 3.0 | 3.0 | 3.0 |
| Carrageenan | — | — | — | — | 0.40 | — |
| Carboxymethyl cellulose | — | — | — | — | 0.60 | 0.60 |
| Hydroxyethylcellulose | 1.2 | 1.3 | 1.2 | 1.0 | — | — |
| Water | 24.64 | 28.54 | 22.04 | 20.24 | 16.85 | 8.36 |
| Saccharin | 0.40 | 0.40 | 0.40 | 0.40 | 0.30 | 0.30 |
| Sodium fluoride | — | — | — | — | — | 0.243 |
| Sodium monofluorophosphate | 0.76 | 0.76 | 0.76 | 0.76 | 0.76 | — |
| Silica abrasive | — | — | 22.0 | 22.0 | 21.3 | 25.5 |
| Hydrated alumina | — | 44.0 | — | — | — | — |
| Dicalcium phosphate | 48.0 | — | — | — | — | — |
| Cetyl pyridinium chloride | 1.0 | 1.0 | 1.0 | 1.0 | — | — |
| Sodium lauryl sulfate | — | — | — | — | 2.4 | 2.4 |
| Zinc citrate | — | — | — | 2.0 | 2.0 | — |
| Tetrapotassium pyrophosphate | — | — | — | — | 2.44 | — |
| Tetrasodium pyrophosphate | — | — | — | — | — | 0.50 |
| Gantrez S-97 | — | — | — | — | 11.4 | — |
| PEG40 hydrogenated castor oil | — | — | 6.0 | 6.0 | — | — |
| PEG40 sorbitan diisostearate | 1.0 | 1.0 | 1.0 | 1.0 | — | — |
| Colorant (TiO2 or dye solution) | — | — | 0.25 | 0.25 | 1.0 | 0.16 |
| NaOH | — | — | 0.50 | 0.50 | 1.25 | — |
| Flavor | 1.0 | 1.0 | 1.0 | 1.0 | 1.2 | 1.0 |

The antiplaque activity of components A, B, C and D each individually combined with component E or F was assessed using a chemostat flow cell model of the type disclosed in the Journal of Dental Research, vol. 73, pp. 1748–1755 (1994).

The Chemostat Flow Cell Model is an in vitro model of dental plaque that is used to assess the potential efficacy of antiplaque agents. The model used a Chemostat (Bioflo 3000), which provided a continuous source of 5 species of oral bacteria; Actinomyces viscosus, Veillionella parvula, Fusobacterium nucleatum, Streptococcus mutans and Streptococcus sanguis. This mixture was pumped through 12 flow cells, each containing four hydroxyapatite disks (Clarkson Chromatography, South Willamsport, Pa.). The disks were previously treated with sterilized saliva for two hours to develop a pellicle-like surface. The plaque bacteria mixture from the Chemostat was pumped over the disk surface at 1 ml/min allowing the bacteria to grow on the disk surface. After 2–3 hours, the disks were treated with a dentifrice slurry. The slurry was made by weighing 10 grams of dentifrice from the composition on one side of the tube with 20 mls of distilled H20. The slurries was allowed to mix completely for 10 minutes after which they were centrifuged @ 10,000 rpm for 10 minutes. The resulting supernatants were used in the treatment process. Each composition was weighed separately, mixed separately and added together 1:1 immediately before disk treatment. Disks were treated 4 times, morning and afternoon for 3 days. Disks were removed from the flow cell and rinsed briefly to remove loose binding bacteria. Formation of bacterial plaque on the disk surfaces was assessed by removing the plaque by treating with 0.025% trypsin for 45 minutes in a 37° water bath. The disks were then vortexed briefly to remove the bacteria and the disk was discarded. The bacterial mix was sonicated for dispersion and the turbidity of the resulting solution was measured at 610 nm in a spectrophotometer. The optical density measurements were then compared to each other and a control.

Optical Density

The combined dentifrice components were assessed for overall plaque inhibition versus a control which was a commercial dentifrice which did not contain an antibacterial agent (designated "Control") which was simultaneously run in the system. The lower the optical density the more effective the antiplaque agent. The results are recorded in Table II below.

TABLE II

| Combined Component Composition | Optical Plaque Density |
|---|---|
| A + E | 0.21 |
| B + E | 0.21 |
| C + E | 0.29 |
| D + F | 0.21 |
| Control | 0.60 |

The results recorded in Table II show that compared to the commercial toothpaste Control, the antiplaque activity of the combined dual component dentifrices was not impaired, each exhibiting significant plaque reduction.

EXAMPLE II

The foaming properties of Component A combined with Component E (adjusted to contain 3% by weight sodium lauryl sulfate) was evaluated using the foaming test described below. For purposes of comparison, 3% by weight of the nonionic surfactant PEG 40 sorbitan distearate was substituted for sodium lauryl sulfate in Component E, designated Dentifrice "X".

The foaming test procedure was performed twice. The foaming test procedure used was as follows:

(A) For Each Test Cell
- 100 grams of 5 mm glass beads were placed into a 500 ml graduated cylinder
- A weighed equal amount of the two dentifrice bases was added to the cylinder to which was added 3 parts deionized water for every one part dentifrice so that each test cell contained the same weight of dentifrice, i.e., between 13–15 grams of toothpaste, and 39–45 grams water. The open end of the cylinders were sealed with a rubber stopper and placed in a foam shaking machine and shaken in 30 cycles per minute for 10 minutes. Thereafter the foam was to drain to the bottom of the cylinder and the total volume in milliliters (ml) occupied by the system (dentifrice slurry, foam and glass beads) was recorded.

Foam volume was obtained by subtracting the original volume occupied by the system prior to shaking. The results of the foam test are recorded in Table III below

TABLE III

| Dual Component Composition | Foam Volume (ml) | |
|---|---|---|
| | Trial 1 | Trial 2 |
| (A + E) | 250 | 300 |
| X | 110 | 115 |

The results recorded in Table III demonstrate that the foamability of the combined dentifrice components A+E in which the anionic surfactant sodium lauryl sulfate was present was more than twice that of the comparative composition X in which a nonionic surfactant was substituted for sodium lauryl sulfate.

What is claimed is:

1. A method of improving the foaming properties of a dual component antiplaque oral composition by preparing the oral composition in a manner in which a first component contains a cationic antibacterial agent and the second component contains a anionic surfactant normally incompatible with the cationic antibacterial agent, preparing the first component free of anionic surfactant and preparing the second component free of cationic antibacterial agent, the foaming properties obtained being twice the foaming properties of a nonionic surfactant in the second component, the first and second components being simultaneously combined for application to the teeth, the first and second components being physically segregated prior to use, the components when mixed upon application to teeth providing substantially unimpaired antiplaque effect with superior foaming properties.

2. The method of claim 1 wherein the cationic antibacterial agent is cetyl pyridinium chloride.

3. The method of claim 1 wherein anionic surfactant is sodium lauryl sulfate.

4. The method of claim 1 wherein the cationic antibacterial agent is included in the first dentifrice component at a concentration of about 0.10 to about 1.5% by weight.

5. The method of claim 1 wherein the anionic surfactant is included in the second dentifrice component at a concentration of about 1.0 to about 5.0% by weight.

* * * * *